United States Patent [19]

Caslavsky et al.

[11] Patent Number: 4,992,260

[45] Date of Patent: Feb. 12, 1991

[54] METHOD OF INHIBITING THE FORMATION OF PLAQUE

[75] Inventors: Vera B. Caslavsky, Lexington, Mass.; Poul Gron, Salem, N.H.

[73] Assignee: Forsyth Dental Infirmary for Children, Boston, Mass.

[21] Appl. No.: 385,572

[22] Filed: Jul. 26, 1989

[51] Int. Cl.$^5$ .................. A61K 7/16; A61K 7/18; A61K 7/22
[52] U.S. Cl. .......................................... 424/52; 424/54
[58] Field of Search .................... 424/52, 54

[56] References Cited

U.S. PATENT DOCUMENTS

| | | | |
|---|---|---|---|
| 4,170,636 | 10/1979 | Engel et al. | 424/52 |
| 4,243,658 | 1/1981 | Chang | 424/52 |
| 4,353,892 | 10/1982 | Caslavsky et al. | 424/52 |
| 4,759,925 | 7/1988 | Gaffar et al. | 424/52 |

FOREIGN PATENT DOCUMENTS

78/00257 12/1978 PCT Int'l Appl. .

OTHER PUBLICATIONS

Gaffar et al., CA 169:176112w(1988) of U.S. 4759925, Jul. 26, 1988.
Gaffar et al., CA 108:600u (1988) of Colloids Surf. 26:109–121 (1987).
Tamura et al., CA 108:5915 (1988) of Caries Res. 21(6): 526–529 (1987).
Caslavska et al., CA 107:83786n (1987) of J. Dent. Res. 66(6): 1159–1161 (1987).
Gron et al., CA 107:12650c (1987) of Caries Res. 21(4): 346–352 (1987).
Caslavsky et al., CA 98:22090e (1983) of U.S. 4,353,892, Oct. 19, 1982.

Primary Examiner—Shep K. Rose
Attorney, Agent, or Firm—Richard P. Crowley

[57] ABSTRACT

A plaque-inhibiting and/or caries-inhibiting, aqueous composition for use in the oral cavity, such as a toothpaste or mouthwash composition, comprising a water carrier and a therapeutic, effective amount of a perfluoroalkyl surfactant having a perfluoroalkyl group and containing a cationic group, such as a cationic perfluoroalkyl thio ether quaternary tri-methyl ammonium compound or an amphoteric perfluoroalkyl anionic-cationic compound.

11 Claims, No Drawings

METHOD OF INHIBITING THE FORMATION OF PLAQUE

BACKGROUND OF THE INVENTION

A wide variety of fluoride compounds have been suggested in oral compositions for use in the oral cavity, such as for use in toothpaste, mouthwash or solutions for professional applications, to inhibit dental caries (see for example U.S. Pat. Nos. 3,029,191 and 4,078,053). Surfactants have been employed in connection with such oral compositions. In particular, a dental caries inhibiting oral composition has been disclosed in U.S. Pat. No. 4,353,892, issued Oct. 12, 1982. The oral composition comprises a caries-inhibiting amount of a water soluble fluoride, such as for example having from 50 to 3000 ppm of the soluble fluoride in combination with a perfluoroalkyl surfactant having a perfluoroalkyl group, a linking group and a hydrophilic group. The combination of the soluble fluoride and the perfluoroalkyl surfactant is used in the oral composition in an amount sufficient to increase the formation of fluoroapatite from enamel-fluoride interactions.

A specific anionic perfluoroalkyl surfactant, Zonyl® FSA, (Zonyl® is a registered trademark of E. I. Du Pont de Nemours & Co.) has been found to be an effective antiplaque additive when employed in oral compositions, either alone or in combination with water soluble fluorides (see U.S. Pat. No. 4,759,925, issued July 26, 1988). As described in the patent, Zonyl® FSA comprises a perfluoroalkyl group and an anionic carboxylic acid salt hydrophilic end group. Zonyl® FSA has been described as being an effective antiplaque employed in oral compositions, such as in toothpaste.

It is desirable to provide for oral compositions which have a combination of both antiplaque and anticaries activity which may be effectively employed alone without the presence of fluorides for effective, therapeutic treatment to reduce plaque and dental caries in patients and which are more antiplaque effective than anionic fluoroalkyl surfactants.

SUMMARY OF THE INVENTION

It has been discovered that perfluoroalkyl surfactants containing a cationic group are effective in reducing plaque and gingivitis in the oral cavity. The perfluoroalkyl surfactants may comprise cationic surfactants, such as ammonium or quaternary ammonium compounds or amphoteric surfactants, which include both anionic, such as carboxylic or carbonyl groups, as well as cationic groups. Such perfluoroalkyl surfactants have been found to be effective antiplaque agents in aqueous oral compositions and also to be effective anticaries agents alone or optionally with water soluble fluoride compounds.

The useful fluoroalkyl surfactants of the invention have the general structural formula:

wherein $R_f$ is a fluoroalkyl group, such as a hydrophobic or oleophobic linear group of $F(CF_2CF_2)_n$ where n is an integer varying from about 2 to 12, such as 3 to 8; A is a linking group; and Z is a hydrophilic group, and where in one embodiment, the hydrophilic group is a cationic group, such as an ammonium or quaternary ammonium group, and in another embodiment, the linking group A or hydrophilic group includes both a cationic and an anionic group, that is, the surfactant is an amphoteric surfactant.

In one embodiment, the perfluoroalkyl surfactant includes Z as $-^+N(R_1)_3$ where $R_1$ is selected from the group consisting of: hydrogen, alkyl group, such as methyl, benzyl, or other hydrocarbon group and where the linking group A includes CH or $CH_2$ groups. Typical cationic surfactants of this embodiment would be represented by commercial surfactants known as Zonyl® FSC having the formula:

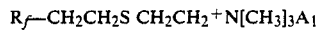

where A is an acid-forming anion, like a halide, phosphate, sulfate, methylsulfate, acetyl or other anion, e.g. a fluoroalkyl thio ether quaternary ammonium methyl sulfate, and Lodyne® S-106 (Lodyne® is a registered trademark of Ciba-Geigy Corp.) which is a cationic fluoroalkyl ammonium chloride.

In another embodiment, an amphoteric perfluoroalkyl surfactant is employed which contains a cationic group and an anionic group. The cationic or anionic group can be at the end of the molecule as the hydrophilic group, e.g. cationic ammonium or quaternary ammonium group or an anionic carboxyl acid group or as a part of the linking group. Amphoteric perfluoroalkyl surfactants include, but are not limited to: Lodyne® S-100, a fluoroalkyl amino carboxylic acid where the cationic group is the amino group and the carboxylic acid is the anionic group; and Lodyne® S-110 which is a fluoroalkyl amino-carboxylic acid, i.e. Lodyne® S-100 with a fluoroalkyl amide (see for example U.S. Pat. Nos. 4,014,926; 4,069,244; 4,081,399; and 4,089,804 for patents describing the Lodyne® surfactants and synergists). Another commercial amphoteric fluoroalkyl surfactant is Zonyl® FSK in which an acetate group is a part of the linking group, and the cationic group is a quaternary ammonium group. Zonyl® FSK has the structural formula:

The surfactants are salt compounds wherein there is an acid- or alkaline-forming cation or anion, depending upon the nature of the end hydrophilic group of the molecule. Suitable cations would include, but not be limited to: ammonium and alkali metal, like lithium; while suitable anions would include, but not be limited to: sulfate, acetate, carboxylates, halides, like chloride, and phosphates.

The perfluoroalkyl surfactants may be used alone as both antiplaque and as anticaries agents or optionally employed in combination with water soluble fluorides. Therapeutic amounts of surfactants may vary, but for example, may typically range from about 0.01% to 3% by weight of the oral composition, and for example, from 0.01% to 0.2% with Zonyl® FSC.

Optionally, the oral composition may contain water soluble fluoride, such as, but not limited to: from 50 ppm to 2000 ppm ionic fluoride derived from sodium fluoride, potassium fluoride, stannous fluoride and ammonium fluoride and mixtures thereof, as well as fluorophosphates and other additives commonly used in dentifrices and mouthwashes, such as for dentifrices polishing agents, flavoring agents, gelling agents and humectants, and for mouthwashes non-toxic alcohols, like ethanol and isopropanol, flavoring agents and antibacterial agents. The cation-containing surfactants may be incorporated and used in place of the anionic surfactants in the oral compositions as described in U.S. Pat. No. 4,759,925 hereby incorporated by reference.

While not wishing to be bound by any particular theory of operation, it is believed that the cation-containing surfactants are particularly effective in reducing plaque on tooth enamel and preventing gingivitis by either restricting the bacterial growth or restricting or preventing the attachment to the negatively charged tooth enamel to aid in forming a barrier layer to the bacteria to prevent growth and in reducing growth, while the anticaries effect alone of the fluoroalkyl surfactants are based on the surfactant effect on the tooth enamel interactions.

The invention will be described for the purposes of illustration only in connection with certain illustrative embodiments; however, it is recognized that changes, additions, modifications and improvements may be made all falling within the spirit and scope of the invention.

DESCRIPTION OF THE EMBODIMENTS

Example 1

The following tests were carried out to show the cariostatic effects in animals of certain surfactants alone and as accelerators in combination with fluorides.

Experimental Procedures

Two animal models were employed, namely 3 to 5-week-old male hamsters and 3-week-old female rats (both supplied by Charles River Breeding Laboratories, Wilmington, Mass.). The animals were divided into groups of 10, each inoculated with Streptococcus mutans (strain 6715) and fed a high sucrose diet (diet 2000, Table I). The hamsters were caged individually, the rats in pairs. The surface active agents with or without fluoride were added to the drinking water given ad libitum. The fluoride concentration was 10 ppm in the case of the hamster and 30 ppm for the rats. Presence of S. mutans was assessed during the study period and immediately prior to sacrifice using selective media (Gold et al., 1973). The animals were killed by carbon dioxide asphyxiation. The heads were defleshed in a beetle colony prior to scoring. Scoring in hamsters, as well as rats, was based on the Keyes (1944) method in which an estimate of the loss of a dentition is made. In evaluating the caries depth, a multiplier of 1 was used if the lesions were limited to the enamel, 2 if the cavitation was progressing into the dentin and 3 if the whole tooth structure was lost in the area. Teeth were scored both unstained as well as stained with Murexide (Navia, 1977).

Sodium fluoride used was analytical reagent grade chemical from Baker Co., Phillipsburg, N.J., while Murexide (assayed at 85% min.) was obtained from Eastman Kodak Co., Rochester, N.Y. Lodyne® S-110 was a commercial grade product. Zonyl® FSC was commercial grade. Carsoquat (Lot #51-28: Lonza Inc., Long Beach, Calif.—75% lauryltrimethylammonium sulfate, 20% myristyltrimethylammonium sulfate, 5% cetyltrimethylammonium sulfate) was tested as a non-fluorocarbon surfactant.

Experiment 1 involved 60 rats. The details are listed in Table II.

Experiment 2 examined the effect of Zonyl® FSC concentrations ranging from 0.001% to 1% as shown in Table III.

Experiment 3 was identical to Experiment 1 but was conducted in hamsters (see Table IV).

In Experiment 4, Zonyl® FSC was tested with and without fluoride in the hamster. Also tested was Carsoquat, a mixture of fluorine-free quaternary ammonium cationic surfactants (see Table V).

The data show that the cariostatic effect is enhanced significantly by combining the fluoride with the cationic fluorosurfactant Zonyl® FSC (Tables II and IV). The enhancement is not apparent when there is essentially no caries in the fluoride group (Table V). The other tested fluorosurfactant, amphoteric Lodyne® S-110, did not show a caries inhibitory effect. It appears that the cationic surface active agent has a better chance to interact with the presumably negatively charged interface than the amphoteric surface active agent. Such interaction could facilitate fluoride deposition. Among the surfactants tested, Zonyl® FSC accelerated deposition of fluoride as firmly bound fluoride in the enamel in vitro the most immediately after topical application. Zonyl® FSC in 0.1% concentration appears marginally caries inhibitory.

The data show that the Zonyl® FSC, both commercial grade and cosmetic grade, in concentrations of 0.1% or less is well tolerated by rats and hamsters. There was no apparent caries inhibition from Zonyl® FSC at concentrations of 0.01% or less.

The Carsoquat (Table V) was tested because it is a fluorine-free mixture of quaternary ammonium surfactants which might be a useful formulation for data comparison. Unfortunately, the fluoride effect was so dominating in this experiment that it was not possible to show an additive effect of Zonyl® FSC or Carsoquat.

Example 2

Hamsters were fed a cariogenic diet and inoculated with S. mutans. A control group received water ad libium while an experimental group received 0.1% Zonyl® FSC fluorosurfactant in the drinking water ad libium. The hamsters were sacrificed after five months and scored for caries.

| Group | Caries Scores | $\overline{X}$ | S.D. |
|---|---|---|---|
| Control | N = 9 | 54.1 | ± 33.3 |
| Zonyl® FSC | N = 5 | 4.95 | ± 1.3 |

Example 3

A clinical trial was conducted to study the effects of an aqueous 0.2% Zonyl® FSC mouthwash on plaque and gingivitis following intensive oral hygiene and a dental prophylaxis to reduce plaque and gingivitis to near zero as possible at the outset of the study. Effects of the active solution were compared to an aqueous placebo. Prior to and during the course of the experiment, the tissues of the oral cavity were carefully examined for any untoward reactions to the mouthwash formulation.

Subjects were examined prior to the start of the study for any pathology that would preclude participation in the experiment. Twenty subjects 18 to 35 years old known to readily form plaque when normal oral hygiene is discontinued were randomly assigned to one of two treatment groups following two weeks of intensive oral hygiene designed to reduce plaque and gingivitis to near zero as possible. During this pre-treatment phase, brushing and flossing were practiced daily using a non-fluoride dentifrice. Mouthwashes were identified by code number to preserve the double blind technique.

Following baseline scoring for plaque and gingivitis, an oral prophylaxis was given on the first day of the 14-day no brushing period. For the next 14 days, subjects were instructed to discontinue all regular oral hygiene procedures, including toothbrushing, use of dental floss and water pressure cleansing devices. Subjects reported to the clinic twice daily, morning and evening, and rinsed under supervision with 10 ml to 15 ml of mouthwash for one minute.

On the morning of the 15th day, the gingivae was scored for gingivitis using a modification of the Gingival Index as follows:

0—Absence of inflammation
1—Mild inflammation; slight change in color, little change in texture, of any portion of, but not the entire marginal or papillary gingival unit
2—Mild inflammation; criteria as above but involving the entire marginal or papillary gingival unit
3—Moderate inflammation; glazing, redness, edema and/or hypertrophy of the marginal or papillary gingival unit
4—Severe inflammation; marked redness, edema and/or hypertrophy of the marginal or papillary gingival unit, spontaneous bleeding, congestion or ulceration Plaque was stained using a fluorescein dye and scored using the Turesky modification of the Quigley-Hein plaque index as follows:

0—No plaque
1—Separate flecks of plaque at the cervical margin of the tooth
2—A thin, continuous band of plaque (up to 1 mm) at the cervical margin
3—A band of plaque wider than 1 mm but covering less than one-third of crown
4—Plaque covering at least one-third but less than two-thirds of the crown
5—Plaque covering two-thirds or more of crown Gingivitis and plaque scores at each examination were recorded on a separate record form. Plaque was collected from the labial and lingual surfaces of the Ramfjord teeth and weighed. Clinical evaluation of the soft tissues for untoward side effects was recorded on a clinical evaluation form.

Mean Gingival Index, Plaque Index and weight of collected plaque in young adults who refrained from tooth brushing but rinsed 2X/day with aqueous 0.2% Zonyl® FSC or H₂O.

|  |  | Treatment | |
|---|---|---|---|
|  |  | Zonyl ® FSC (N = 10) | H₂O (N = 7) |
| Gingival | B | 1.36 ± 0.66 | 1.72 ± 0.25 |
| Index | L | 1.39 ± 0.52 | 1.59 ± 0.38 |
| Plaque | B | 2.79 ± 0.82 | 3.08 ± 0.83 |
| Index | L | 2.36 ± 0.69 | 2.86 ± 0.52 |
| Plaque Weight (mg) | | 10.30 ± 3.51 | 13.30 ± 7.39 |

The clinical data establish that cationic FSC is an effective antigingivitis and antiplaque agent.

Example 4

Animal tests were conducted to determine the anticaries effectiveness of an amphoteric and a cationic fluoroalkyl surfactant with and without fluoride (see Table VI).

Example 5

Zonyl® FSC and Lodyne® 106 were tested at various concentration levels as an antiplaque-antibacteria agent against *S. mutans* in saliva (see Table VII).

Procedure for study of surface active agents on salivary bacteria

Prepare blood plates—40 gm Trypticase Soy Agar base and 950 ml distilled water. Autoclave and once cooled, add 50 ml of sheep blood and agitate gently. Pour into sterile plates and allow to cool.

Prepare discs—Cut filter paper with a one-hole punch and sterilize by placing them in hot air oven.

Seed plates—Collect saliva and pipette 1 ml on each plate and spread evenly over the surface with a glass rod. Let dry for a few minutes.

Samples—Moisten discs with 0.01 ml of desired solution and then place disc on prepared plate. Incubate for 24° at 37° C.

Results—Measure the zone of inhibition—diameter of area in which there is no growth (see Tables VI–VII).

TABLE I

| Composition of Diet 2000: | |
|---|---|
| confectionary sugar | 56% |
| skim milk | 28% |
| white wheat flour | 6% |
| yeast | 4% |
| alfalfa | 3% |
| liver | 1% |
| NaCL | 2% |

TABLE II

Experiment #1: Treatments, number of animals and mean Caries Index Scores (CIS) ± Standard Deviation in rats receiving 0.1% Zonyl ® FSC or 0.1% Lodyne ® S-110 in the drinking water with or without 30 ppm fluoride from NaF. Duration of experiment 95 days.

| Group | Drinking Water | Number Surviving | Mean CIS | Stat.Eval.* |
|---|---|---|---|---|
| I | H₂O | 10 | 84.6 ± 50.0 | A |
| II | 30 ppm F | 10 | 26.8 ± 9.4 | C |
| III | 30 ppm F + 0.1% Lodyne S-110 | 10 | 28.6 ± 18.1 | C |
| IV | 30 ppm F + 0.1% Zonyl FSC | 10 | 6.3 ± 6.7 | D |
| V | 0.1% Lodyne S-110 | 10 | 62.9 ± 35.0 | AB |
| VI | 0.1% Zonyl FSC | 10 | 33.2 ± 17.7 | BC |

Zonyl FSC and Lodyne S-110 commercial grade.
*Statistical Evaluation based on Fisher's Least Significant DIfference +-Test. Means with the same letter are not significantly different.

TABLE III

Experiment #2: Treatments, number of surviving animals and mean Caries Index Scores (CIS) ± Standard Deviation in rats receiving varying concentrations of Zonyl ® FSC in the drinking water. Duration of experiment 96 days.

| Group | Drinking Water | Number Survivng | Mean CIS |
|---|---|---|---|
| I | H$_2$O | 10 | 67.1 ± 28.5 |
| II | 1% Zonyl FSC | 0 | — |
| III | 0.1% Zonyl FSC | 9 | 51.8 ± 18.6 |
| IV | 0.01% Zonyl FSC | 10 | 69.2 ± 17.2 |
| V | 0.001% Zonyl FSC | 10 | 45.4 ± 14.2 |

TABLE IV

Experiment #3: Treatment, number of animals and mean Caries Index Scores (CIS) ± Standard Deviation in hamsters receiving 0.1% Zonyl ® FSC or 0.1% Lodyne ® S-110 in the drinking water with or without 10 ppm fluoride from NaF. Duration of experiment 129 days.

| Group | Drinking Water | Number Surviving | Mean CIS | Stat. Eval.* |
|---|---|---|---|---|
| I | H$_2$O | 10 | 149.0 ± 29.6 | A |
| II | 10 ppm F | 10 | 58.5 ± 44.8 | B |
| III | 10 ppm F + 0.1% Lodyne S-110 | 10 | 60.6 ± 33.6 | B |
| IV | 10 ppm F + 0.1% Zonyl FSC | 10 | 15.4 ± 13.2 | C |
| V | 0.1% Lodyne S-110 | 10 | 146.5 ± 40.3 | A |
| VI | 0.1% Zonyl FSC | 10 | 98.5 ± 27.0 | A |

Zonyl FSC and Lodyne S-110 commercial grade.
*Statistical Evaluation based on Fisher's Significant Difference +-Test. Means with the same letter are not significantly different.

TABLE V

Experiment #4: Treatments, number of surviving animals and mean Caries Index Scores (CIS) ± Standard Deviation in hamsters receiving 0.1% Zonyl FSC or 0.1% Carsoquat in the drinking water with or without 10 ppm fluoride from NaF. Duration of experiment 133 days.

| Group | Drinking Water | Number Surviving | Mean CIS | Stat.Eval." |
|---|---|---|---|---|
| I | H$_2$O | 11* | 39.6 ± 25.1 | A |
| II | 10 ppm F | 10 | 1.57 ± 0.86 | C |
| III | 10 ppm F + 0.1% Carsoquat | 10 | 2.35 ± 1.62 | C |
| IV | 10 ppm F + 0.1% Zonyl FSC | 9 | 2.44 ± 1.61 | C |
| V | 0.1% Carsoquat | 9 | 19.9 ± 14.4 | B |
| VI | 0.1% Zonyl FSC | 8 | 24.2 ± 12.3 | AB |

*This group started with 12 animals; all the others with 10
Carsoquat commercial grade.
"Statistical evaluation based on Fisher's Least Significant Difference +-Test. Means with the same letter are not significantly different.

TABLE VI

Results of Tests of Following Compounds on Saliva

| Sample | Concentration | Zone of Inhibition (in diameter) |
|---|---|---|
| Lodyne 106 | 100% | 2.60 |
| Zonyl FSC | 50% | 1.55 |
| Zonyl FSC • | 0.1% | 0.75 |
|  | 0.01% | 0.75 |
|  | 1.0% | 1.0 |
| Cetyl pyridinium chloride | 1.0% | 0.94 |
|  | 0.1% | 0.83 |
| Chlorohexidine | 0.1% | 0.64 |
|  | 1.0% | 0.85 |

TABLE VII

| Solution | Conc. | Bacteria Growth Streptococcus mutans 6715 | | | | | |
|---|---|---|---|---|---|---|---|
|  |  | TSA | TSA | TSA | MSA | TSA | |
| Zonyl FSC | 0.05% | — | — | — | — | ± | ± |
|  | 0.1 | ± | ± | ± | ± | ± | ± |
|  | 0.2 | ++ | ++ | ++ | ++ | ++ | ++ |
|  | 0.4 | ++ | ++ | ++ | ++ | ++ | +++ |
|  | 0.6 | ++ | ++ | ++ | ++ | ++ | +++ |
| Lodyne S106 | 0.1 | ± | ± | ± | ± | ± | ± |
|  | 0.2 | ++ | ++ | ++ | ++ | ++ | + |
|  | 0.4 | 0 | ++ | ++ | 0 | ++ | ++ |
|  | 0.6 | 0 | ++ | ++ | 0 | ++ | ++ |
| Lodyne S110 | 0.1 | ± | ± | ± | ± | ± | ± |
|  | 0.2 | ± | ± | ± | ± | ± | ± |
|  | 0.4 | 0 | + | + | 0 | ± | + |
|  | 0.6 | 0 | + | + | 0 | ± | + |

±ambiguous
++positively restricts the growth
—does not restrict growth

What is claimed is:

1. A method of inhibiting the formation of plaque on the tooth enamel of a subject which method comprises: contacting the teeth of the subject with a composition which consists essentially of an effective, anti-plaque amount of a fluoroalkyl thioether alkyl quaternary ammonium surfactant.

2. The method of claim 1 wherein the surfactant comprises a trimethyl quaternary ammonium compound.

3. The method of claim 1 wherein the composition comprises a dentifrice composition and which comprises: water; a polishing agent; a gelling agent; a flavoring agent; and a humectant.

4. The method of claim 1 wherein the composition comprises a mouth rinse composition which comprises water, a pharmaceutically-acceptable alcohol, a flavoring agent and an antibacterial agent.

5. The method of claim 1 wherein the fluoroalkyl surfactant is present in an amount of from about 0.01% to 3.0% by weight of the composition.

6. The method of claim 1 which includes a water soluble fluoride compound in a therapeutic amount to reduce caries.

7. The method of claim 1 wherein the fluoroalkyl group comprises a $F(CF_2CF_2)_n$ group where n is an integer which ranges from about 2 to 12.

8. The method of claim 1 wherein the fluoroalkyl thioether alkyl quaternary ammonium surfactant compound has the structural formula:

$$R_f\text{—}CH_2CH_2SCH_2CH_2N^+(CH_3)_3A_1$$

wherein $R_f$ is a fluoroalkyl group, and $A_1$ is an acid-forming anion.

9. The method of claim 1 wherein the composition includes from about 50 to 2,000 ppm of a water soluble fluoride selected from the group consisting of: sodium fluoridge, potassium fluoride, stannous fluoride, ammonium fluoride and mixtures thereof.

10. A method of inhibiting the formation of plaque on the tooth enamel of a subject, which method comprises:
contacting the teeth of the subject with an aqueous oral composition which consists essentially of from about 0.01% to 3.0% by weight of a fluoroalkyl thio ether trimethyl quaternary ammonium surfactant compound as an antiplaque agent.

11. The method of claim 10 wherein the oral composition includes a caries-inhibiting amount of a water soluble fluoride compound.

* * * * *